US009955965B2

(12) United States Patent
Chen et al.

(10) Patent No.: US 9,955,965 B2
(45) Date of Patent: May 1, 2018

(54) SWITCH BLOCK CONTROL ASSEMBLY OF A MEDICAL DEVICE

(71) Applicant: COVIDIEN LP, Mansfield, MA (US)

(72) Inventors: Xingrui Chen, Glastonbury, CT (US); David A. Nicholas, Trumbull, CT (US); Matthew J. Chowaniec, Middletown, CT (US); Michael A. Zemlok, Prospect, CT (US); Blaine Williams, East Haven, CT (US); Anthony Calderoni, Bristol, CT (US)

(73) Assignee: Covidien LP, Mansfield, MA (US)

( * ) Notice: Subject to any disclaimer, the term of this patent is extended or adjusted under 35 U.S.C. 154(b) by 949 days.

(21) Appl. No.: 13/913,727

(22) Filed: Jun. 10, 2013

(65) Prior Publication Data

US 2014/0012238 A1    Jan. 9, 2014

Related U.S. Application Data

(60) Provisional application No. 61/669,263, filed on Jul. 9, 2012.

(51) Int. Cl.
*A61B 1/00* (2006.01)
*A61B 1/04* (2006.01)
(Continued)

(52) U.S. Cl.
CPC ...... *A61B 17/068* (2013.01); *A61B 17/07207* (2013.01); *A61B 17/10* (2013.01);
(Continued)

(58) Field of Classification Search
CPC ............ A61B 18/1442; A61B 18/1445; A61B 18/1447; A61B 2018/145;
(Continued)

(56) References Cited

U.S. PATENT DOCUMENTS

| 2,777,340 A | 1/1957 | Hettwer et al. |
| 2,957,353 A | 10/1960 | Babacz |
| (Continued) | | |

FOREIGN PATENT DOCUMENTS

| EP | 0634144 | 1/1995 |
| EP | 1690502 | 8/2006 |
| (Continued) | | |

OTHER PUBLICATIONS

International Search Report corresponding to PCT/US2005/027266, completed May 30, 2008 and dated Jun. 18, 2008; (2 pp.).

(Continued)

*Primary Examiner* — Anhtuan T Nguyen
*Assistant Examiner* — William Chou

(57) ABSTRACT

The present disclosure provides a surgical device, comprising: a jaw assembly defining a first longitudinal axis and including a first jaw and a second jaw moveable relative to the first jaw; an elongated body defining a second longitudinal axis and coupled to a proximal end of the jaw assembly, wherein the jaw assembly is configured to articulate about an articulation axis transverse to the second longitudinal axis relative to the elongated body; a handle assembly coupled to a proximal end of the elongated body and comprising at least one motor mechanically coupled to the jaw assembly; and a control assembly coupled to the handle assembly, the control assembly including a first control button, a second control button, a first rocker device disposed about the first control button and configured to rotate thereabout, and a second rocker device disposed about the second control button and configured to rotate thereabout.

7 Claims, 15 Drawing Sheets

(51) Int. Cl.
*A61B 1/06* (2006.01)
*A61B 17/068* (2006.01)
*A61B 17/10* (2006.01)
*A61B 17/32* (2006.01)
*A61B 17/072* (2006.01)
*A61B 17/11* (2006.01)
*A61B 17/115* (2006.01)
*A61B 17/00* (2006.01)

(52) U.S. Cl.
CPC .............. *A61B 17/32* (2013.01); *A61B 17/115* (2013.01); *A61B 17/1114* (2013.01); *A61B 17/1155* (2013.01); *A61B 2017/0046* (2013.01); *A61B 2017/00367* (2013.01); *A61B 2017/00398* (2013.01); *A61B 2017/00734* (2013.01); *A61B 2017/1132* (2013.01)

(58) Field of Classification Search
CPC ...... A61B 2018/1452; A61B 2018/146; A61B 2018/1462; A61B 2017/00017; A61B 2017/00212; A61B 17/068; A61B 17/08; A61B 17/10; A61B 17/32
USPC ....... 606/1, 51, 52, 167, 205, 206, 207, 208, 606/209, 209 D; 600/564; 227/175.1
See application file for complete search history.

(56) References Cited

U.S. PATENT DOCUMENTS

| | | | |
|---|---|---|---|
| 3,111,328 A | 11/1963 | Di Rito et al. | |
| 3,695,058 A | 10/1972 | Keith, Jr. | |
| 3,734,515 A | 5/1973 | Dudek | |
| 3,759,336 A | 9/1973 | Marcovitz et al. | |
| 4,162,399 A | 7/1979 | Hudson | |
| 4,606,343 A | 8/1986 | Conta et al. | |
| 4,705,038 A | 11/1987 | Sjostrom et al. | |
| 4,874,181 A | 10/1989 | Hsu | |
| 5,129,118 A | 7/1992 | Walmesley | |
| 5,129,570 A | 7/1992 | Schulze et al. | |
| 5,152,744 A | 10/1992 | Krause et al. | |
| 5,312,023 A | 5/1994 | Green et al. | |
| 5,326,013 A | 7/1994 | Green et al. | |
| 5,350,355 A | 9/1994 | Sklar | |
| 5,383,874 A | 1/1995 | Jackson et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,400,267 A | 3/1995 | Denen et al. | |
| 5,413,267 A | 5/1995 | Solyntjes et al. | |
| 5,467,911 A * | 11/1995 | Tsuruta ............. | A61B 17/0682 227/175.1 |
| 5,476,379 A | 12/1995 | Disel | |
| 5,487,499 A | 1/1996 | Sorrentino et al. | |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,542,594 A | 8/1996 | McKean et al. | |
| 5,562,239 A | 10/1996 | Boiarski et al. | |
| 5,653,374 A | 8/1997 | Young et al. | |
| 5,667,517 A | 9/1997 | Hooven | |
| 5,704,534 A | 1/1998 | Huitema et al. | |
| 5,713,505 A | 2/1998 | Huitema | |
| 5,779,130 A | 7/1998 | Alesi et al. | |
| 5,782,397 A | 7/1998 | Koukline | |
| 5,820,009 A | 10/1998 | Melling et al. | |
| 5,863,159 A | 1/1999 | Lasko | |
| 5,908,427 A | 6/1999 | McKean et al. | |
| 5,954,259 A | 9/1999 | Viola et al. | |
| 5,964,774 A | 10/1999 | McKean et al. | |
| 5,993,454 A | 11/1999 | Longo | |
| 6,017,354 A | 1/2000 | Culp et al. | |
| 6,045,560 A | 4/2000 | McKean et al. | |
| 6,090,123 A | 7/2000 | Culp et al. | |
| 6,129,547 A | 10/2000 | Cise et al. | |
| 6,264,087 B1 | 7/2001 | Whitman | |
| 6,302,311 B1 | 10/2001 | Adams et al. | |
| 6,315,184 B1 | 11/2001 | Whitman | |
| 6,321,855 B1 | 11/2001 | Barnes | |
| 6,329,778 B1 | 12/2001 | Culp et al. | |
| 6,343,731 B1 | 2/2002 | Adams et al. | |
| 6,348,061 B1 | 2/2002 | Whitman | |
| 6,368,324 B1 | 4/2002 | Dinger et al. | |
| 6,434,507 B1 | 8/2002 | Clayton et al. | |
| 6,443,973 B1 | 9/2002 | Whitman | |
| 6,461,372 B1 | 10/2002 | Jensen et al. | |
| 6,488,197 B1 | 12/2002 | Whitman | |
| 6,491,201 B1 | 12/2002 | Whitman | |
| 6,533,157 B1 | 3/2003 | Whitman | |
| 6,537,280 B2 | 3/2003 | Dinger et al. | |
| 6,610,066 B2 | 8/2003 | Dinger et al. | |
| 6,611,793 B1 | 8/2003 | Burnside et al. | |
| 6,698,643 B2 | 3/2004 | Whitman | |
| 6,699,177 B1 | 3/2004 | Wang et al. | |
| 6,716,233 B1 | 4/2004 | Whitman | |
| 6,792,390 B1 | 9/2004 | Burnside et al. | |
| 6,817,508 B1 | 11/2004 | Racenet et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,959,852 B2 | 11/2005 | Shelton, IV et al. | |
| 6,964,363 B2 | 11/2005 | Wales et al. | |
| 6,981,628 B2 | 1/2006 | Wales | |
| 6,981,941 B2 | 1/2006 | Whitman et al. | |
| 7,032,798 B2 | 4/2006 | Whitman et al. | |
| 7,055,731 B2 | 6/2006 | Shelton, IV et al. | |
| 7,077,856 B2 | 7/2006 | Whitman | |
| 7,111,769 B2 | 9/2006 | Wales et al. | |
| 7,143,923 B2 | 12/2006 | Shelton, IV et al. | |
| 7,143,925 B2 | 12/2006 | Shelton, IV et al. | |
| 7,143,926 B2 | 12/2006 | Shelton, IV et al. | |
| 7,147,138 B2 | 12/2006 | Shelton, IV | |
| 7,246,734 B2 | 7/2007 | Shelton, IV | |
| 7,328,828 B2 | 2/2008 | Ortiz et al. | |
| 7,364,061 B2 | 4/2008 | Swayze et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,416,101 B2 | 8/2008 | Shelton, IV et al. | |
| 7,419,080 B2 | 9/2008 | Smith et al. | |
| 7,422,139 B2 | 9/2008 | Shelton, IV et al. | |
| 7,431,189 B2 | 10/2008 | Shelton, IV et al. | |
| 7,441,684 B2 | 10/2008 | Shelton, IV et al. | |
| 7,448,525 B2 | 11/2008 | Shelton, IV et al. | |
| 7,464,846 B2 | 12/2008 | Shelton, IV et al. | |
| 7,464,847 B2 | 12/2008 | Viola et al. | |
| 7,464,849 B2 | 12/2008 | Shelton et al. | |
| 7,481,347 B2 | 1/2009 | Roy | |
| 7,487,899 B2 | 2/2009 | Shelton, IV et al. | |
| 7,549,564 B2 | 6/2009 | Boudreaux | |
| 7,568,603 B2 | 8/2009 | Shelton, IV et al. | |
| 7,588,176 B2 | 9/2009 | Timm et al. | |
| 7,637,409 B2 | 12/2009 | Marczyk | |
| 7,641,093 B2 | 1/2010 | Doll et al. | |
| 7,644,848 B2 | 1/2010 | Swayze et al. | |
| 7,670,334 B2 | 3/2010 | Hueil et al. | |
| 7,673,780 B2 | 3/2010 | Shelton, IV et al. | |
| 7,721,931 B2 | 5/2010 | Shelton, IV et al. | |
| 7,740,159 B2 | 6/2010 | Shelton, IV et al. | |
| 7,743,960 B2 | 6/2010 | Whitman et al. | |
| 7,758,613 B2 | 7/2010 | Whitman | |
| 7,766,210 B2 | 8/2010 | Shelton, IV et al. | |
| 7,770,773 B2 | 8/2010 | Whitman et al. | |
| 7,770,775 B2 | 8/2010 | Shelton et al. | |
| 7,799,039 B2 | 9/2010 | Shelton, IV et al. | |
| 7,802,712 B2 | 9/2010 | Milliman et al. | |
| 7,819,896 B2 | 10/2010 | Racenet | |
| 7,845,537 B2 | 12/2010 | Shelton, IV et al. | |
| 7,905,897 B2 | 3/2011 | Whitman et al. | |
| 7,918,230 B2 | 4/2011 | Whitman et al. | |

(56) References Cited

U.S. PATENT DOCUMENTS

| | | | |
|---|---|---|---|
| 7,947,034 B2 | 5/2011 | Whitman | |
| 7,951,071 B2 | 5/2011 | Whitman et al. | |
| 7,963,433 B2 | 6/2011 | Whitman et al. | |
| 7,967,178 B2 | 6/2011 | Scirica et al. | |
| 7,992,758 B2 | 8/2011 | Whitman et al. | |
| 8,016,855 B2 | 9/2011 | Whitman et al. | |
| 8,020,743 B2 | 9/2011 | Shelton, IV | |
| 8,157,151 B2 | 4/2012 | Ingmanson et al. | |
| 8,186,555 B2 | 5/2012 | Shelton, IV et al. | |
| 8,220,367 B2 | 7/2012 | Hsu | |
| 8,241,322 B2 | 8/2012 | Whitman et al. | |
| 8,292,888 B2 | 10/2012 | Whitman | |
| 8,357,144 B2 | 1/2013 | Whitman et al. | |
| 8,365,972 B2 | 2/2013 | Aranyi | |
| 8,372,057 B2 | 2/2013 | Cude et al. | |
| 8,391,957 B2 | 3/2013 | Carlson et al. | |
| 2003/0130677 A1* | 7/2003 | Whitman | A61B 17/072 606/167 |
| 2004/0111012 A1 | 6/2004 | Whitman | |
| 2005/0033337 A1* | 2/2005 | Muir | A61B 17/32009 606/167 |
| 2005/0162389 A1* | 7/2005 | Obermeyer | G05G 9/047 345/161 |
| 2006/0142656 A1 | 6/2006 | Malackowski et al. | |
| 2007/0029363 A1 | 2/2007 | Popov | |
| 2007/0084897 A1 | 4/2007 | Shelton, IV et al. | |
| 2007/0102472 A1 | 5/2007 | Shelton, IV | |
| 2007/0175949 A1 | 8/2007 | Shelton, IV et al. | |
| 2007/0175950 A1 | 8/2007 | Shelton, IV et al. | |
| 2007/0175951 A1 | 8/2007 | Shelton, IV et al. | |
| 2007/0175955 A1 | 8/2007 | Shelton, IV et al. | |
| 2008/0029570 A1 | 2/2008 | Shelton, IV et al. | |
| 2008/0029573 A1 | 2/2008 | Shelton, IV et al. | |
| 2008/0029574 A1 | 2/2008 | Shelton, IV et al. | |
| 2008/0029575 A1 | 2/2008 | Shelton, IV et al. | |
| 2008/0058801 A1 | 3/2008 | Taylor et al. | |
| 2008/0109012 A1 | 5/2008 | Falco et al. | |
| 2008/0185419 A1 | 8/2008 | Smith et al. | |
| 2008/0200940 A1* | 8/2008 | Eichmann | A61B 17/32006 606/169 |
| 2008/0208195 A1 | 8/2008 | Shores et al. | |
| 2008/0234767 A1* | 9/2008 | Salmon | A61M 16/1095 607/2 |
| 2008/0251561 A1 | 10/2008 | Eades et al. | |
| 2008/0255607 A1 | 10/2008 | Zemlok | |
| 2008/0262654 A1 | 10/2008 | Omori et al. | |
| 2009/0076504 A1* | 3/2009 | Schnitzler | A61B 18/1402 606/45 |
| 2009/0090763 A1 | 4/2009 | Zemlok et al. | |
| 2009/0099876 A1 | 4/2009 | Whitman | |
| 2009/0182193 A1 | 7/2009 | Whitman et al. | |
| 2009/0209990 A1 | 8/2009 | Yates et al. | |
| 2010/0007402 A1* | 1/2010 | Chamuczynski | H03K 17/97 327/510 |
| 2011/0121049 A1 | 5/2011 | Malinouskas et al. | |
| 2011/0218522 A1 | 9/2011 | Whitman | |
| 2011/0253765 A1 | 10/2011 | Nicholas et al. | |
| 2012/0253329 A1 | 10/2012 | Zemlok et al. | |

FOREIGN PATENT DOCUMENTS

| | | |
|---|---|---|
| EP | 1736112 | 12/2006 |
| EP | 1769754 | 4/2007 |
| EP | 1813203 | 8/2007 |
| EP | 1943958 | 7/2008 |
| EP | 1943976 | 7/2008 |
| EP | 2027819 | 2/2009 |
| EP | 2055243 | 5/2009 |
| EP | 2098170 | 9/2009 |
| EP | 2100561 | 9/2009 |
| WO | WO 2000/072760 | 12/2000 |
| WO | WO 2000/072765 | 12/2000 |
| WO | WO 2003/026511 | 4/2003 |
| WO | WO 2003/077769 | 9/2003 |
| WO | WO 2004/107989 | 12/2004 |
| WO | WO 2006/042210 | 4/2006 |
| WO | WO 2007/014355 | 2/2007 |
| WO | WO 2007/026354 | 3/2007 |
| WO | WO 2008/131362 | 10/2008 |
| WO | WO 2008/133956 | 11/2008 |
| WO | WO 2009/039506 | 3/2009 |
| WO | WO 2009/132359 | 10/2009 |

OTHER PUBLICATIONS

Extended European Search Report corresponding to EP 08 25 3184.9, completed Feb. 12, 2009 and dated Feb. 27, 2009; (3 pp.).
Extended European Search Report corresponding to EP 10 25 0228.3, completed May 20, 2010 and dated Jun. 1, 2010; (6 pp.).
Extended European Search Report corresponding to EP 10 25 2037.6, completed Mar. 1, 2011 and dated Mar. 9, 2011; (3 pp.).
Extended European Search Report corresponding to EP 10 25 1968.3, completed on Jul. 4, 2011 and dated Jul. 14, 2011; (12 pp.).
Extended European Search Report corresponding to EP 11 15 2266.0, completed Jul. 15, 2011 and dated Jul. 28, 2011; (3 pp.).
Extended European Search Report corresponding to EP 11 25 0462.6, completed Jul. 20, 2011 and dated Jul. 28, 2011; (6 pp.).
Extended European Search Report corresponding to EP 11 25 0771.0, completed Feb. 7, 2012 and dated Feb. 17, 2012; (3 pp.).
Extended European Search Report corresponding to EP 06 78 8914.7, completed May 3, 2012 and dated May 11, 2012; (8 pp.).
Partial European Search Report corresponding to EP 12 18 6177.7, completed Jan. 30, 2013 and dated Feb. 12, 2013; (6 pp.).
Extended European Search Report corresponding to EP 08 25 2703.7, completed Oct. 23, 2008 and dated Oct. 31, 2008; (7 pp.).

* cited by examiner

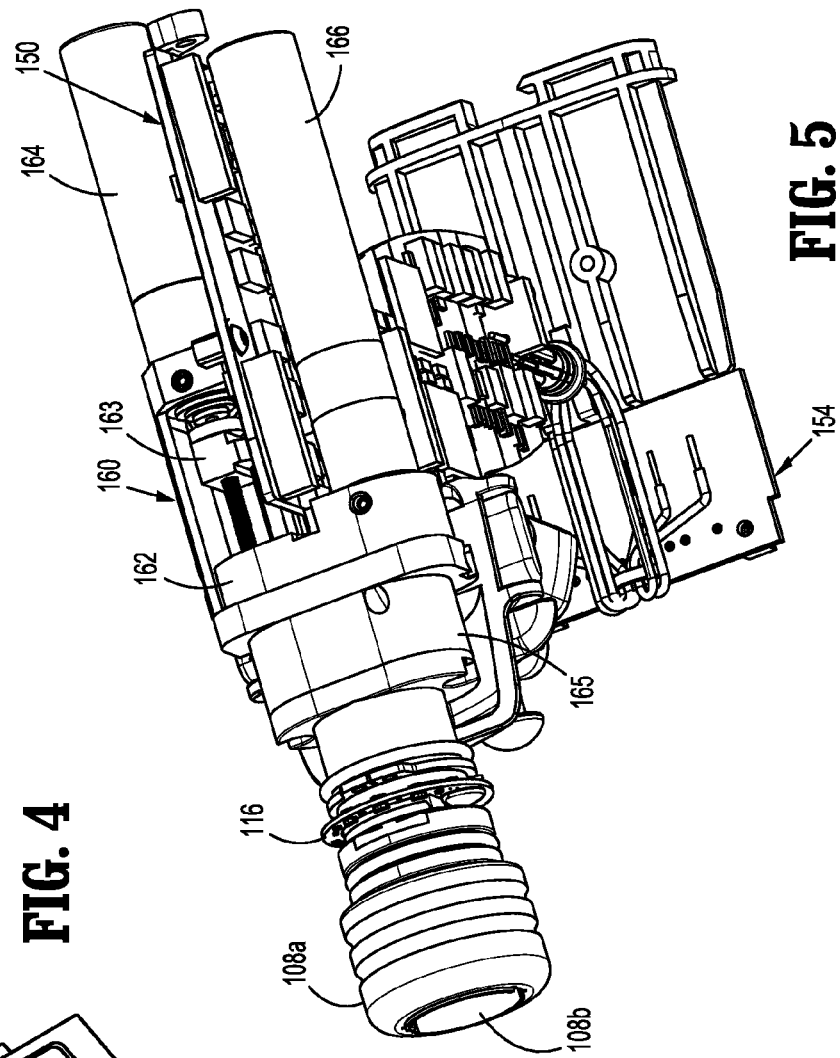
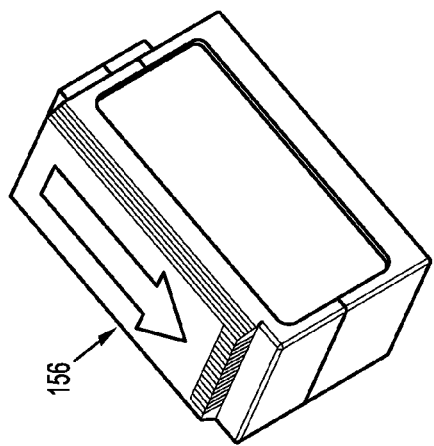
FIG. 4
FIG. 5

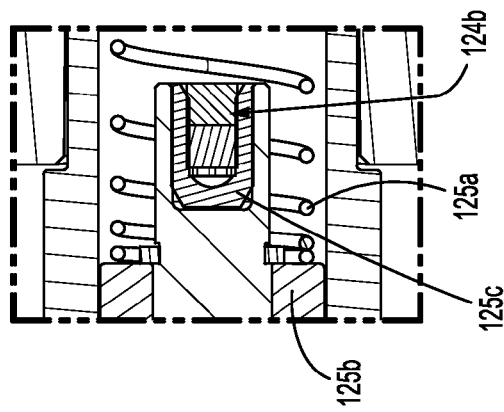
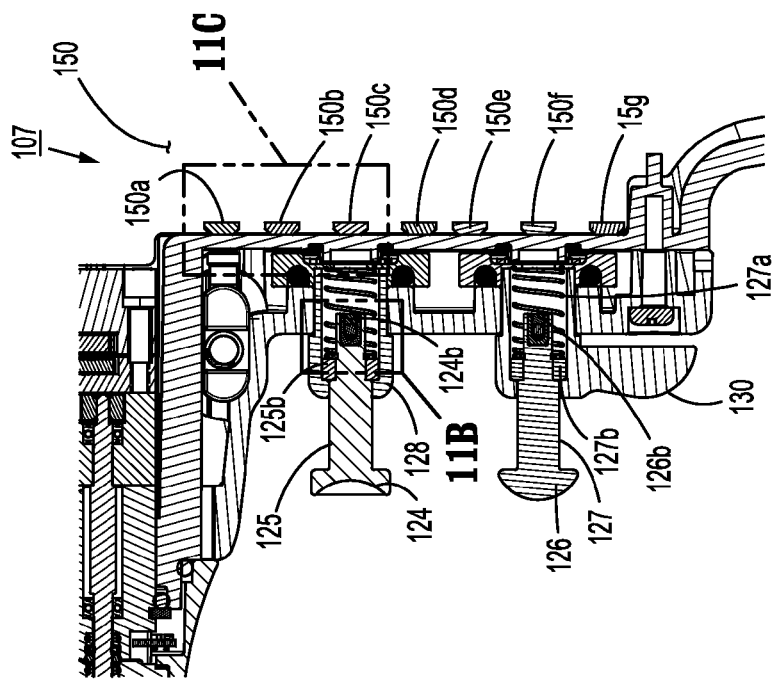
FIG. 11A
FIG. 11B
FIG. 11C

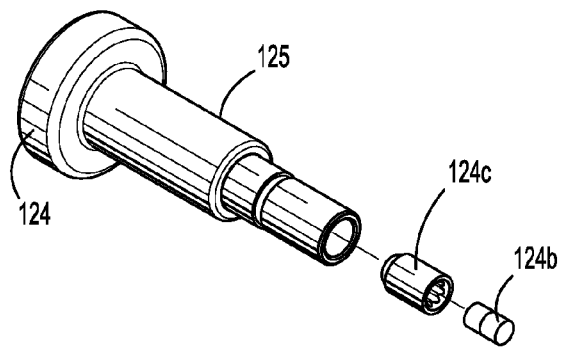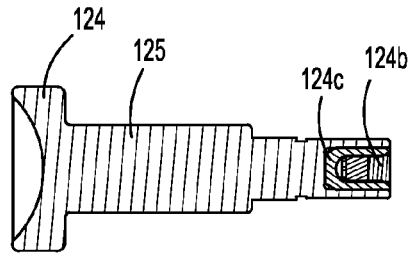
FIG. 14A  FIG. 14B
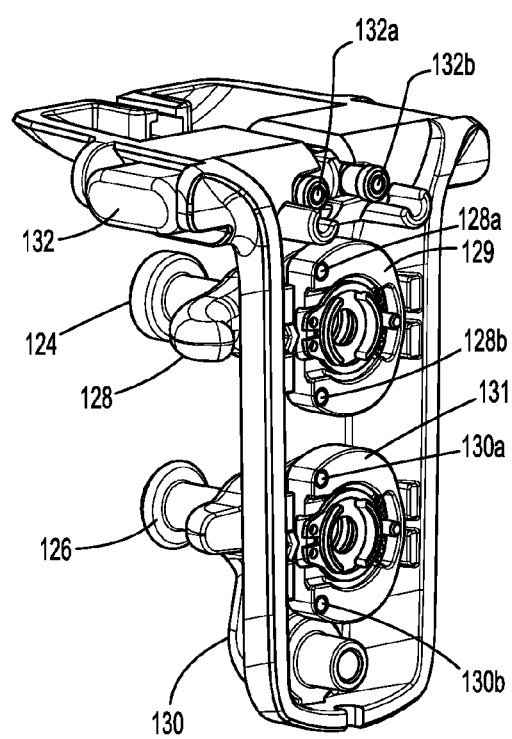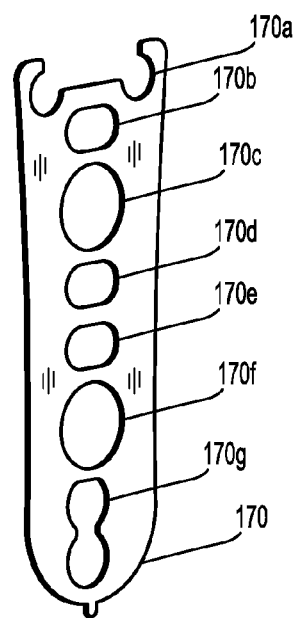
FIG. 15A

SWITCH BLOCK CONTROL ASSEMBLY OF A MEDICAL DEVICE

CROSS REFERENCE TO RELATED APPLICATION

The present application claims the benefit of and priority to U.S. Provisional Application Ser. No. 61/669,263, filed on Jul. 9, 2012, the entire contents of which are incorporated herein by reference.

BACKGROUND

1. Technical Field

The present disclosure relates to surgical devices. More specifically, the present disclosure relates to control assemblies for use on a powered, rotating and/or articulating surgical device or handle assembly.

2. Background of Related Art

One type of surgical device is a linear clamping, cutting and stapling device. Such a device may be employed in a surgical procedure to resect a cancerous or anomalous tissue from a gastro-intestinal tract. Conventional linear clamping, cutting and stapling instruments include a pistol grip-styled structure having an elongated shaft and distal portion. The distal portion includes a pair of scissors-styled gripping elements, which clamp the open ends of the colon closed. In this device, one of the two scissors-styled gripping elements, such as the anvil portion, moves or pivots relative to the overall structure, whereas the other gripping element remains fixed relative to the overall structure. The actuation of this scissoring device (the pivoting of the anvil portion) is controlled by a grip trigger maintained in the handle.

In addition to the scissoring device, the distal portion also includes a stapling mechanism. The fixed gripping element of the scissoring mechanism includes a staple cartridge receiving region and a mechanism for driving the staples up through the clamped end of the tissue against the anvil portion, thereby sealing the previously opened end. The scissoring elements may be integrally formed with the shaft or may be detachable such that various scissoring and stapling elements may be interchangeable.

A number of surgical device manufacturers have developed product lines with proprietary powered drive systems for operating and/or manipulating the surgical device. In many instances the surgical devices include a powered handle assembly, which is reusable, and a disposable end effector or the like that is selectively connected to the powered handle assembly prior to use and then disconnected from the end effector following use in order to be disposed of or in some instances sterilized for re-use.

Many of the existing end effectors for use with many of the existing powered surgical devices and/or handle assemblies are driven by a linear force. For examples, end effectors for performing endo-gastrointestinal anastomosis procedures, end-to-end anastomosis procedures and transverse anastomosis procedures, each typically require a linear driving force in order to be operated. As such, these end effectors are not compatible with surgical devices and/or handle assemblies that use a rotary motion to deliver power or the like.

In order to make the linear driven end effectors compatible with powered surgical devices and/or handle assemblies that use a rotary motion to deliver power, a need exists for adapters and/or adapter assemblies to interface between and interconnect the linear driven end effectors with the powered rotary driven surgical devices and/or handle assemblies.

Many of these powered rotary driven surgical devices and/or handle assemblies are complex devices, including many parts and requiring extensive labor to assemble. Accordingly, a need exists to develop powered rotary driven surgical devices and/or handle assemblies that incorporate fewer parts, are less labor intensive to assemble and ultimately more economical to manufacture.

SUMMARY

The present disclosure relates to surgical adapters and/or adapter assemblies for use between and for interconnecting a powered, rotating and/or articulating surgical device or handle assembly and an end effector for clamping, cutting and/or stapling tissue.

The present disclosure provides a surgical device, comprising: a jaw assembly defining a first longitudinal axis and including a first jaw and a second jaw moveable relative to the first jaw; an elongated body defining a second longitudinal axis and coupled to a proximal end of the jaw assembly, wherein the jaw assembly is configured to articulate about an articulation axis transverse to the second longitudinal axis relative to the elongated body; a handle assembly coupled to a proximal end of the elongated body and comprising at least one motor mechanically coupled to the jaw assembly; and a control assembly coupled to the handle assembly, the control assembly including a first control button, a second control button, a first rocker device disposed about the first control button and configured to rotate thereabout, and a second rocker device disposed about the second control button and configured to rotate thereabout.

In additional aspects, actuation of the first control button moves the second jaw in approximation relative to the first jaw and actuating the second control button moves the second jaw away from the first jaw.

In further aspects, actuation of the first rocker switch is configured to articulate the jaw assembly about the articulation axis.

In further aspects, actuation of the second rocker switch is configured to rotate the jaw assembly about the second longitudinal axis relative to the elongated body.

In additional aspects, the first control button includes a first magnetic element, the second control button includes a second magnetic element, the first rocker device includes third and fourth magnetic elements, and the second rocker device includes fifth and sixth magnetic elements.

In additional aspects, the handle assembly comprises a plurality of sensors configured to detect proximity of the first, second, third, fourth, fifth, and sixth magnetic elements.

In further aspects, the control assembly comprises a magnetic shield having a plurality of openings aligned with the plurality of sensors, the magnetic shield configured to shield the third, fourth, fifth, and sixth magnetic elements from respect sensors until the first and second rocker devices are actuated.

BRIEF DESCRIPTION OF THE DRAWINGS

Embodiments of the present disclosure are described herein with reference to the accompanying drawings, wherein:

FIG. 4 is a perspective view of a battery for use in the surgical device of FIGS. 1-3 according to the present disclosure;

FIG. 5 is a perspective view of the surgical device of FIGS. 1-3, with a housing thereof removed according to the present disclosure;

FIG. 11A are cross-sectional views of the control assembly of FIG. 9 and enlarged portions of interest thereof according to the present disclosure;

FIG. 11B is an enlarged view of the indicated area of detail of FIG. 11A;

FIG. 11C is an enlarged view of the indicated area of detail of FIG. 11A;

FIG. 14A is a perspective, disassembled view of a control button according to the present disclosure;

FIG. 14B is a side, cross-sectional view of the control button according to the present disclosure;

FIG. 15A is a perspective, partially-disassembled view of the control assembly of FIG. 9 according to the present disclosure;

DETAILED DESCRIPTION OF EMBODIMENTS

A surgical device, in accordance with an embodiment of the present disclosure, is generally designated as 100, and is in the form of a powered hand held electromechanical instrument configured for selective attachment thereto of a plurality of different end effectors that are each configured for actuation and manipulation by the powered hand held electromechanical surgical instrument.

Figure 1:
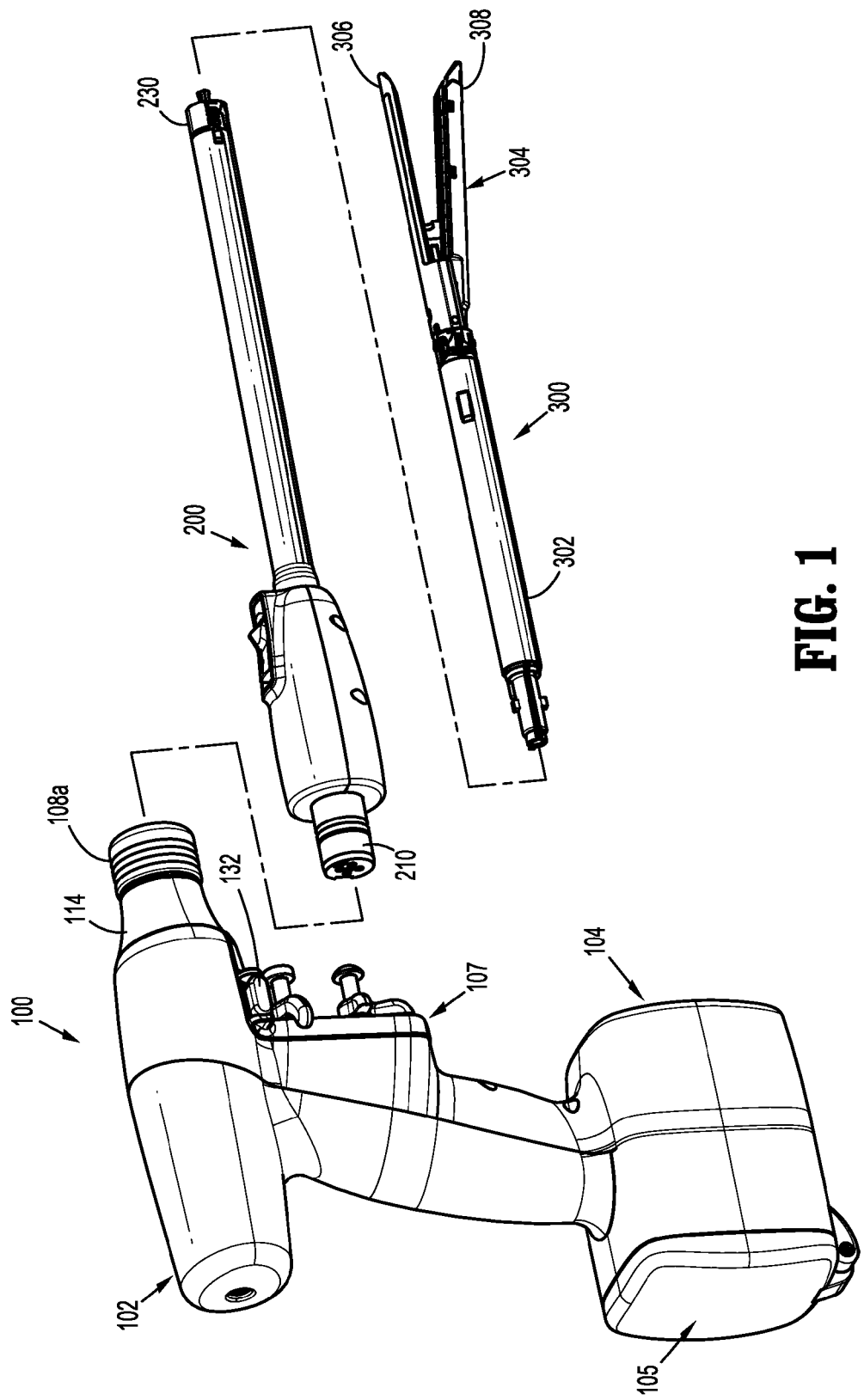
FIG. 1 is a perspective view, with parts separated, of a surgical device and adapter, in accordance with an embodiment of the present disclosure, illustrating a connection thereof with an end effector according to the present disclosure.

As illustrated in FIG. 1, surgical device 100 is configured for selective connection with an adapter 200, and, in turn, adapter 200 is configured for selective connection with an end effector or single use loading unit 300.

Figure 2:
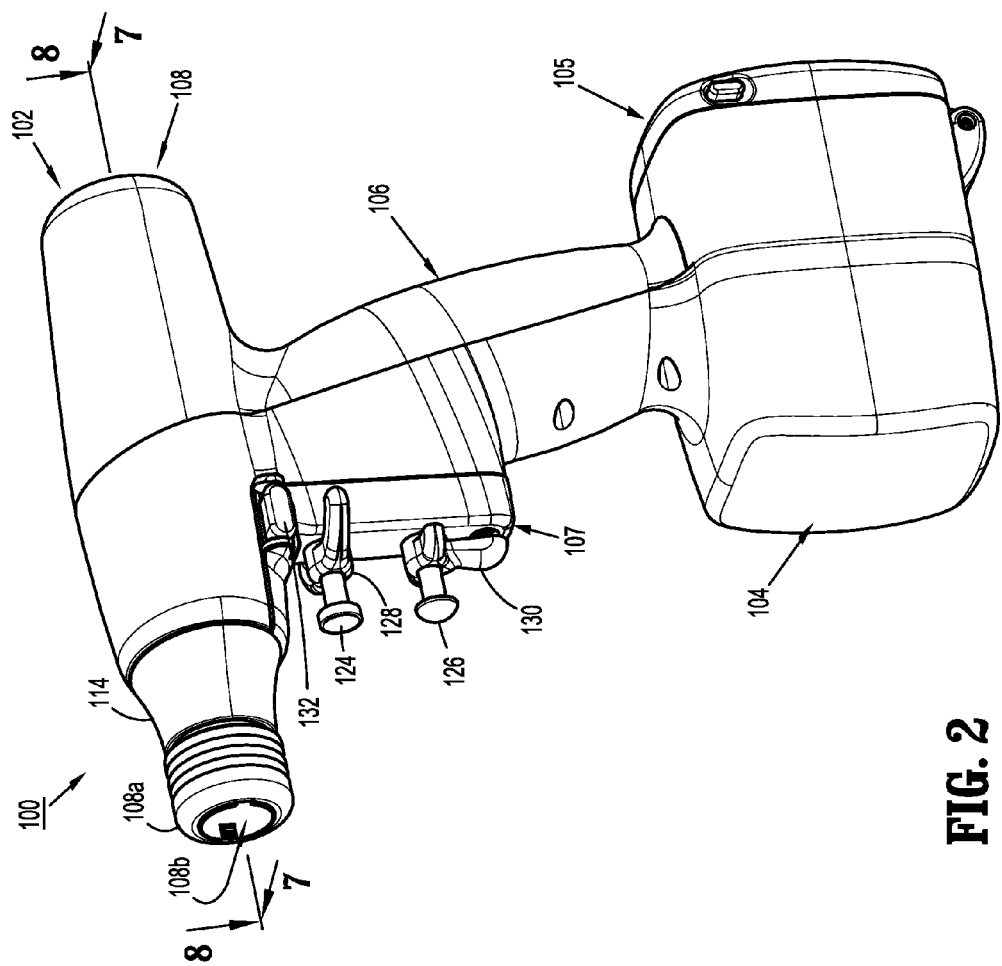
FIG. 2 is a perspective view of the surgical device of FIG. 1 according to the present disclosure.
Figure 3:
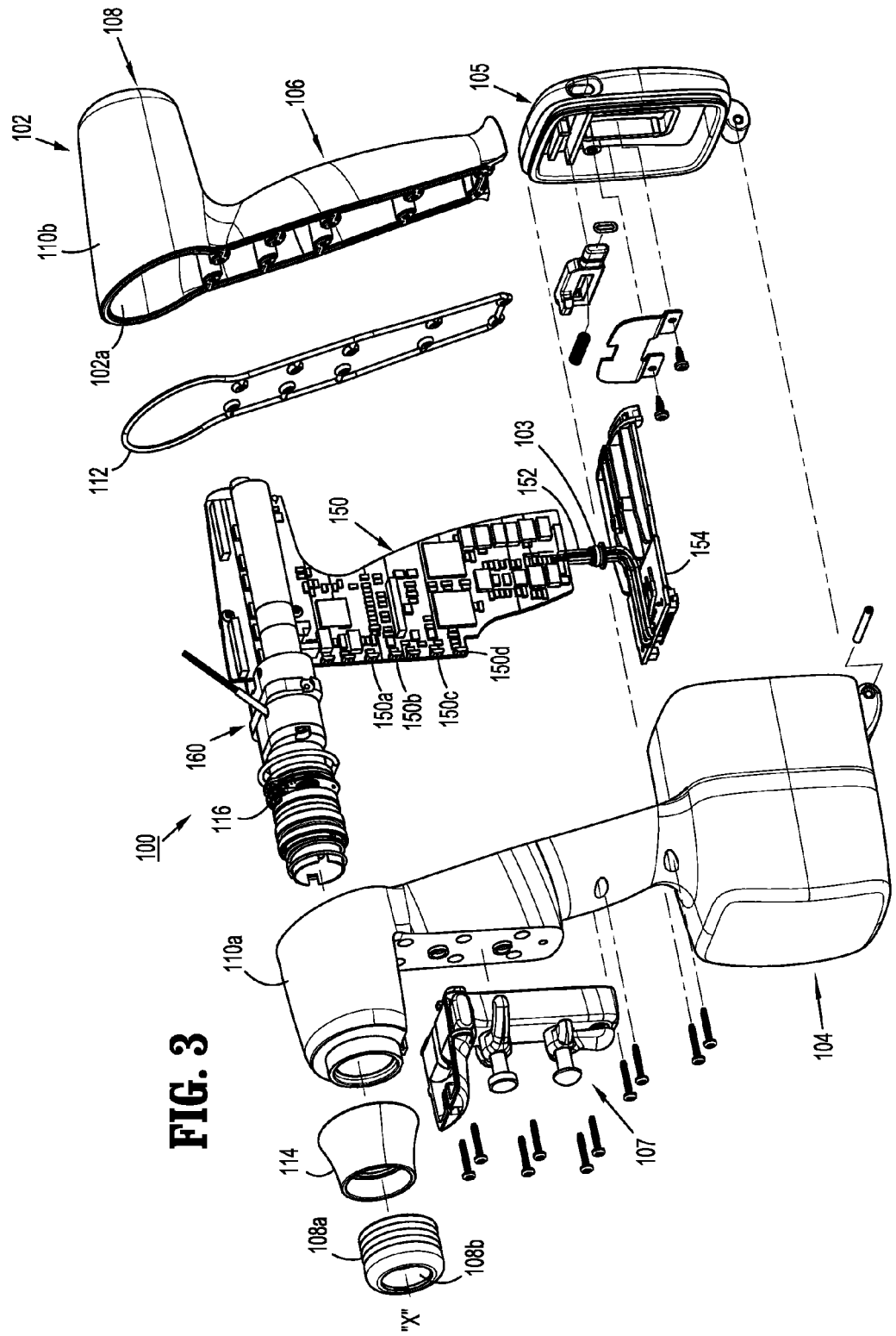
FIG. 3 is a perspective view, with parts separated, of the surgical device of FIGS. 1 and 2 according to the present disclosure.

As illustrated in FIGS. 1-3, surgical device 100 includes a handle housing 102 having a lower housing portion 104, an intermediate housing portion 106 extending from and/or supported on lower housing portion 104, and an upper housing portion 108 extending from and/or supported on intermediate housing portion 106. Intermediate housing portion 106 and upper housing portion 108 are separated into a distal half-section 110a that is integrally formed with and extending from the lower portion 104, and a proximal half-section 110b connectable to distal half-section 110a by a plurality of fasteners. When joined, distal and proximal half-sections 110a, 110b define a handle housing 102 having a cavity 102a therein in which a circuit board 150 and a drive mechanism 160 is situated.

Distal and proximal half-sections 110a, 110b are divided along a plane that traverses a longitudinal axis "X" of upper housing portion 108, as seen in FIG. 1.

Handle housing 102 includes a gasket 112 extending completely around a rim of distal half-section and/or proximal half-section 110a, 110b and being interposed between distal half-section 110a and proximal half-section 110b. Gasket 112 seals the perimeter of distal half-section 110a and proximal half-section 110b. Gasket 112 functions to establish an air-tight seal between distal half-section 110a and proximal half-section 110b such that circuit board 150 and drive mechanism 160 are protected from sterilization and/or cleaning procedures.

In this manner, the cavity 102a of handle housing 102 is sealed along the perimeter of distal half-section 110a and proximal half-section 110b yet is configured to enable easier, more efficient assembly of circuit board 150 and a drive mechanism 160 in handle housing 102.

Intermediate housing portion 106 of handle housing 102 provides a housing in which circuit board 150 is situated. Circuit board 150 is configured to control the various operations of surgical device 100, as will be set forth in additional detail below.

Lower housing portion 104 of surgical device 100 defines an aperture (not shown) formed in an upper surface thereof and which is located beneath or within intermediate housing portion 106. The aperture of lower housing portion 104 provides a passage through which wires 152 pass to electrically interconnect electrical components (a battery 156, as illustrated in FIG. 4, a circuit board 154, as illustrated in FIG. 3, etc.) situated in lower housing portion 104 with electrical components (circuit board 150, drive mechanism 160, etc.) situated in intermediate housing portion 106 and/or upper housing portion 108.

Handle housing 102 includes a gasket 103 disposed within the aperture of lower housing portion 104 (not shown) thereby plugging or sealing the aperture of lower housing portion 104 while allowing wires 152 to pass therethrough. Gasket 103 functions to establish an air-tight seal between lower housing portion 106 and intermediate housing portion 108 such that circuit board 150 and drive mechanism 160 are protected from sterilization and/or cleaning procedures.

As shown, lower housing portion 104 of handle housing 102 provides a housing in which a rechargeable battery 156, is removably situated. Battery 156 is configured to supply power to any of the electrical components of surgical device 100. Lower housing portion 104 defines a cavity (not shown) into which battery 156 is inserted. Lower housing portion 104 includes a door 105 pivotally connected thereto for closing cavity of lower housing portion 104 and retaining battery 156 therein.

With reference to FIGS. 3 and 5, distal half-section 110a of upper housing portion 108 defines a nose or connecting portion 108a. A nose cone 114 is supported on nose portion 108a of upper housing portion 108. Nose cone 114 is fabricated from a transparent material. An illumination member 116 is disposed within nose cone 114 such that illumination member 116 is visible therethrough. Illumination member 116 is in the form of a light emitting diode printed circuit board (LED PCB). Illumination member 116 is configured to illuminate multiple colors with a specific color pattern being associated with a unique discrete event.

Upper housing portion 108 of handle housing 102 provides a housing in which drive mechanism 160 is situated. As illustrated in FIG. 5, drive mechanism 160 is configured to drive shafts and/or gear components in order to perform the various operations of surgical device 100. In particular, drive mechanism 160 is configured to drive shafts and/or gear components in order to selectively move tool assembly 304 of end effector 300 (see FIGS. 1 and 20) relative to proximal body portion 302 of end effector 300, to rotate end effector 300 about a longitudinal axis "X" (see FIG. 3) relative to handle housing 102, to move anvil assembly 306 relative to cartridge assembly 308 of end effector 300, and/or to fire a stapling and cutting cartridge within cartridge assembly 308 of end effector 300.

The drive mechanism 160 includes a selector gearbox assembly 162 that is located immediately proximal relative to adapter 200. Proximal to the selector gearbox assembly 162 is a function selection module 163 having a first motor 164 that functions to selectively move gear elements within the selector gearbox assembly 162 into engagement with an input drive component 165 having a second motor 166.

As illustrated in FIGS. 1-4, and as mentioned above, distal half-section 110a of upper housing portion 108 defines a connecting portion 108a configured to accept a corresponding drive coupling assembly 210 of adapter 200.

Figure 6:
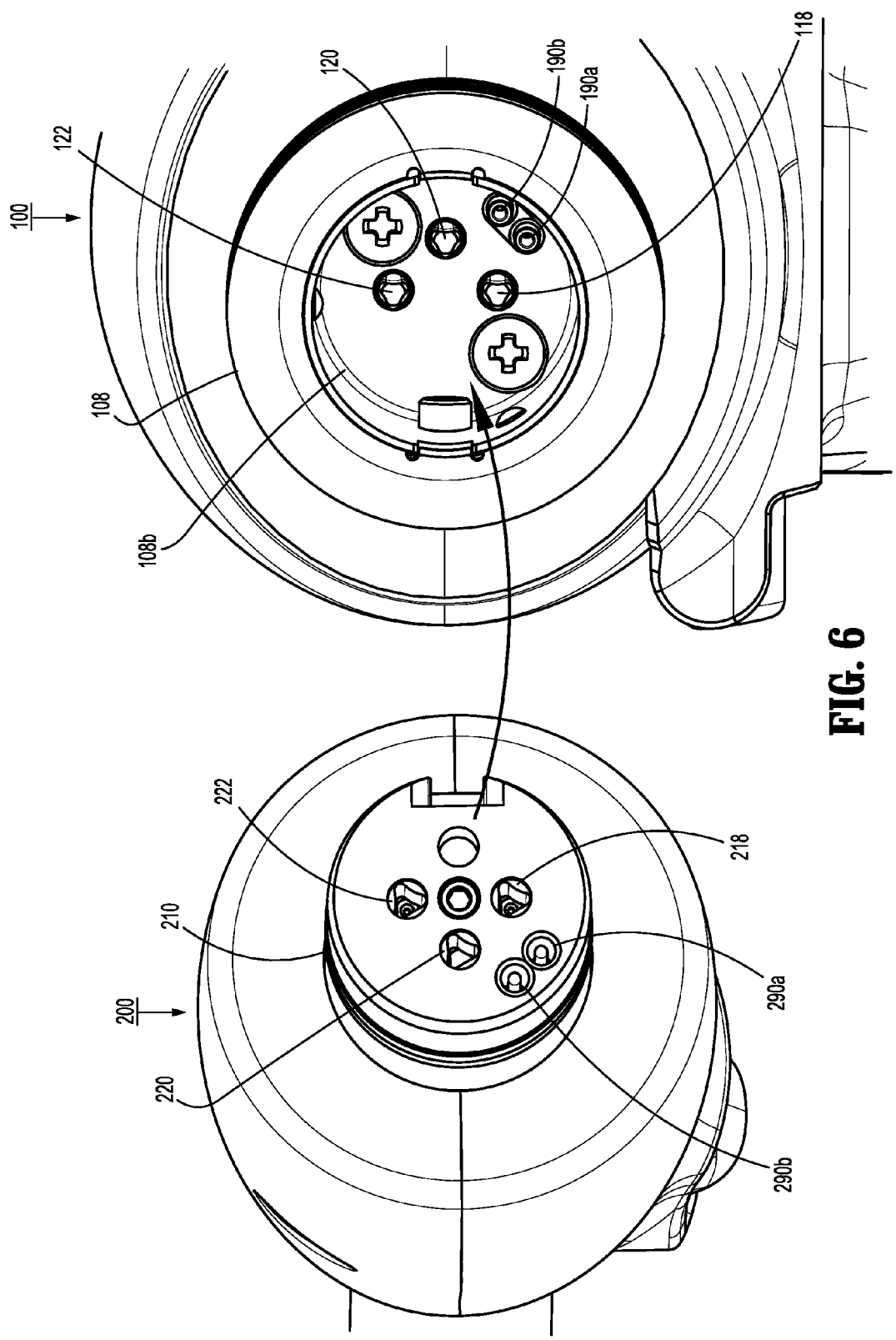
FIG. 6 is a perspective view of the connecting ends of each of the surgical device and the adapter, illustrating a connection therebetween according to the present disclosure.
Figure 7:
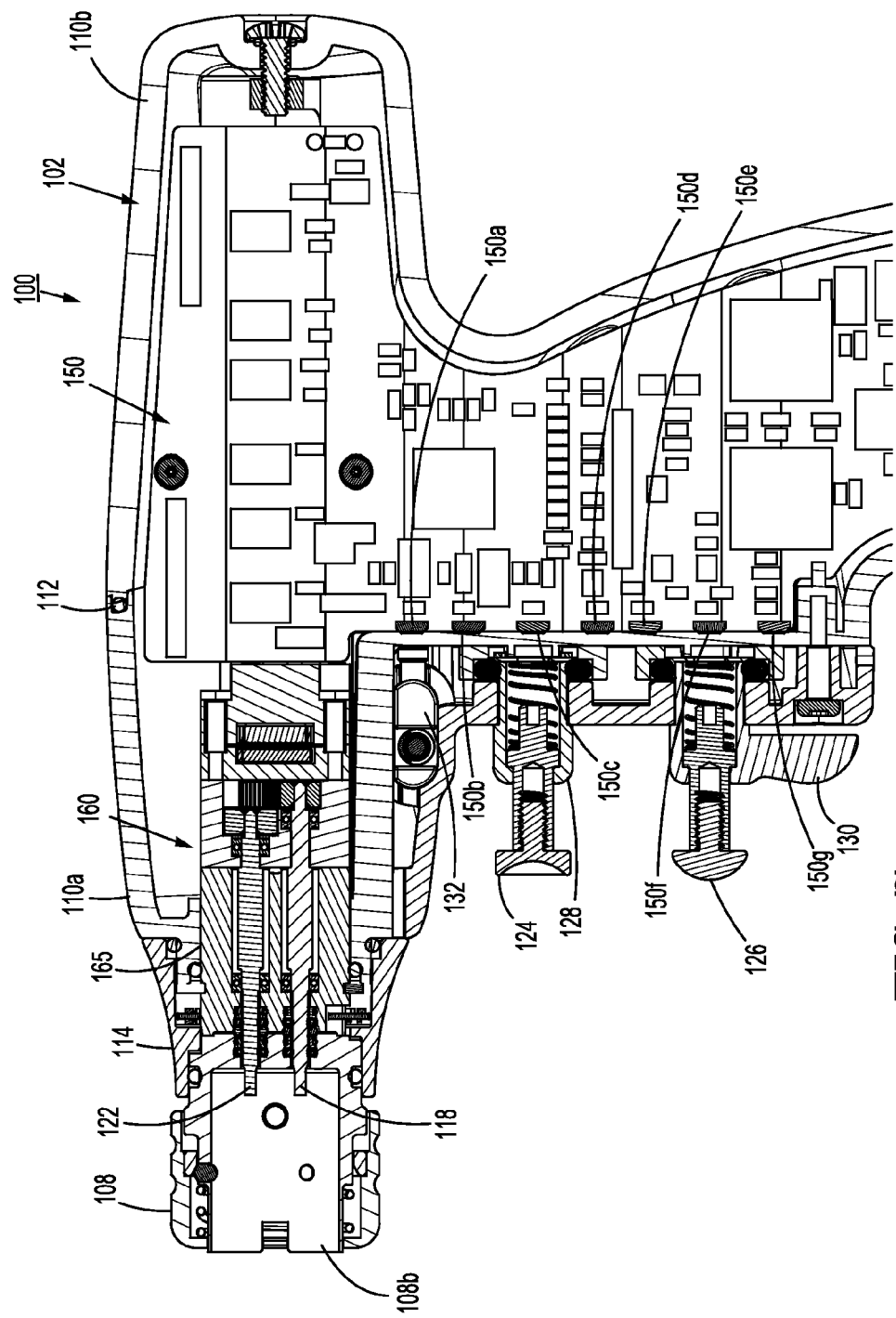
FIG. 7 is a cross-sectional view of the surgical device of FIGS. 1-3, as taken through 7-7 of FIG. 2 according to the present disclosure.
Figure 8:
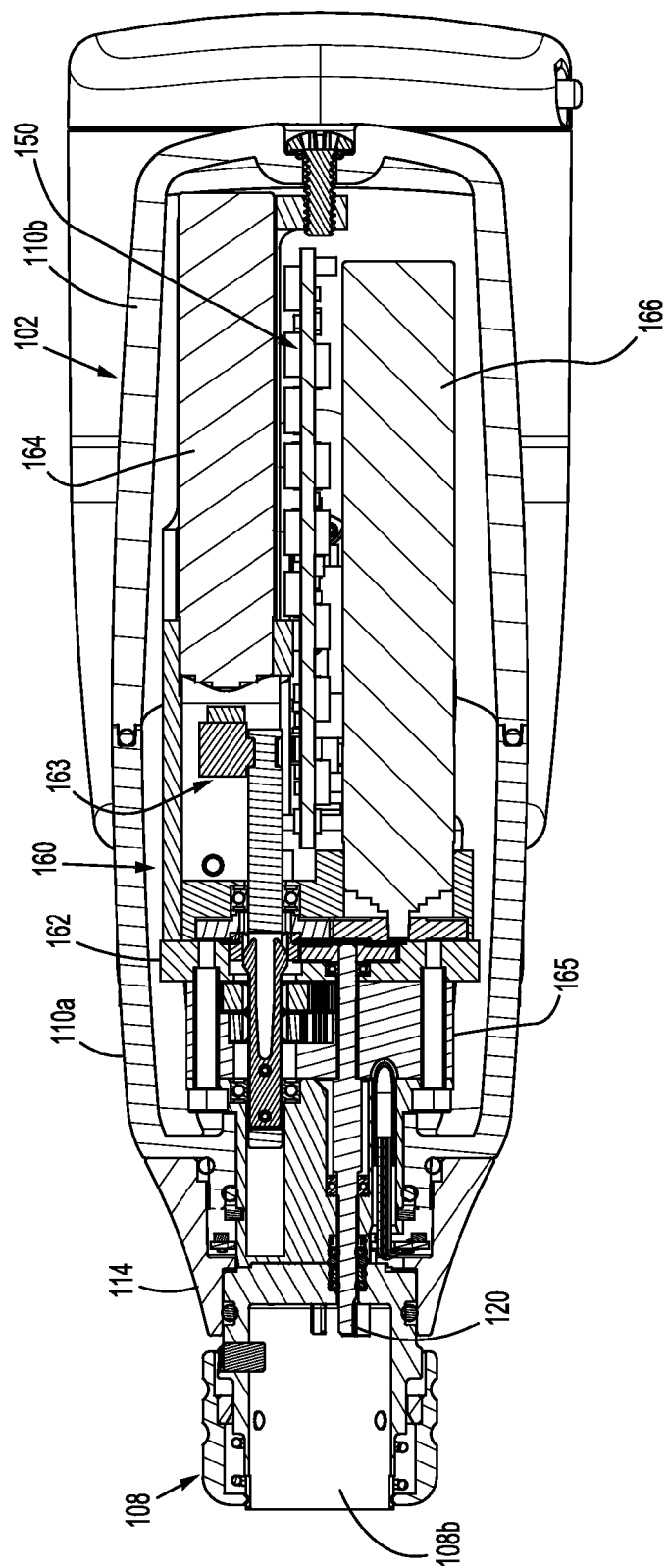
FIG. 8 is a cross-sectional view of the surgical device of FIGS. 1-3, as taken through 8-8 of FIG. 2 according to the present disclosure.

As illustrated in FIGS. 6-8, connecting portion 108a of surgical device 100 has a cylindrical recess 108b that receives a drive coupling assembly 210 of adapter 200 when adapter 200 is mated to surgical device 100. Connecting portion 108a houses three rotatable drive connectors 118, 120, 122.

When adapter 200 is mated to surgical device 100, each of rotatable drive connectors 118, 120, 122 of surgical device 100 couples with a corresponding rotatable connector sleeve 218, 220, 222 of adapter 200. (see FIG. 6). In this regard, the interface between corresponding first drive connector 118 and first connector sleeve 218, the interface between corresponding second drive connector 120 and second connector sleeve 220, and the interface between corresponding third drive connector 122 and third connector sleeve 222 are keyed such that rotation of each of drive connectors 118, 120, 122 of surgical device 100 causes a corresponding rotation of the corresponding connector sleeve 218, 220, 222 of adapter 200.

The mating of drive connectors 118, 120, 122 of surgical device 100 with connector sleeves 218, 220, 222 of adapter 200 allows rotational forces to be independently transmitted via each of the three respective connector interfaces. The drive connectors 118, 120, 122 of surgical device 100 are configured to be independently rotated by drive mechanism 160. In this regard, the function selection module 163 of drive mechanism 160 selects which drive connector or connectors 118, 120, 122 of surgical device 100 is to be driven by the input drive component 165 of drive mechanism 160.

Since each of drive connectors 118, 120, 122 of surgical device 100 has a keyed and/or substantially non-rotatable interface with respective connector sleeves 218, 220, 222 of adapter 200, when adapter 200 is coupled to surgical device 100, rotational force(s) are selectively transferred from drive mechanism 160 of surgical device 100 to adapter 200.

The selective rotation of drive connector(s) 118, 120 and/or 122 of surgical device 100 allows surgical device 100 to selectively actuate different functions of end effector 300. As will be discussed in greater detail below, selective and independent rotation of first drive connector 118 of surgical device 100 corresponds to the selective and independent opening and closing of tool assembly 304 of end effector 300, and driving of a stapling/cutting component of tool assembly 304 of end effector 300. Also, the selective and independent rotation of second drive connector 120 of surgical device 100 corresponds to the selective and independent articulation of tool assembly 304 of end effector 300 transverse to longitudinal axis "X" (see FIG. 3). Additionally, the selective and independent rotation of third drive connector 122 of surgical device 100 corresponds to the selective and independent rotation of end effector 300 about longitudinal axis "X" (see FIG. 3) relative to handle housing 102 of surgical device 100.

As mentioned above and as illustrated in FIGS. 5 and 8, drive mechanism 160 includes a selector gearbox assembly 162; a function selection module 163, located proximal to the selector gearbox assembly 162, that functions to selectively move gear elements within the selector gearbox assembly 162 into engagement with second motor 166. Thus, drive mechanism 160 selectively drives one of drive connectors 118, 120, 122 of surgical device 100 at a given time.

As illustrated in FIGS. 1-3 and FIG. 9-18, handle housing 102 supports a control assembly 107 on a distal surface or side of intermediate housing portion 108. The control assembly 107 is a fully-functional mechanical subassembly that can be assembled and tested separately from the rest of the instrument 100 prior to coupling thereto.

Control assembly 107, in cooperation with intermediate housing portion 108, supports a pair of finger-actuated control buttons 124, 126 and a pair rocker devices 128, 130 within a housing 107a. The control buttons 124, 126 are coupled to extension shafts 125, 127 respectively. In particular, control assembly 107 defines an upper aperture 124a for slidably receiving the extension shaft 125, and a lower aperture 126a for slidably receiving the extension shaft 127.

The control assembly 107 and its components (e.g., control buttons 124, 126 and rocker devices 128, 130) my be formed from low friction, self-lubricating, lubricious plastics or materials or coatings covering the moving components to reduce actuation forces, key component wear, elimination of galling, smooth consistent actuation, improved component and assembly reliability and reduced clearances for a tighter fit and feel consistency. This includes the use of plastic materials in the bushings, rocker journals, plunger bushings, spring pockets, retaining rings and slider components as described in further detail below. Molding the components in plastic also provides net-shape or mesh-shaped components with all of these performance attributes. Plastic components eliminate corrosion and bi-metal anodic reactions under electrolytic conditions such as autoclaving, steam sterilizations and cleaning. Press fits with lubricious plastics and materials also eliminate clearances with minimal strain or functional penalties on the components when compared to similar metal components.

Suitable materials for forming the components of the control assembly 107 include, but are not limited to, polyamines, polyphenylene sulfides, polyphthalamides, polyphenylsulfones, polyether ketones, polytetrafluoroethylenes, and combinations thereof. These components may be used in the presence or absence of lubricants and may also include additives for reduced wear and frictional forces.

With reference to FIGS. 9-11C, the rocker devices 128, 130 are disposed about the control buttons 124, 126, namely, extension shafts 125, 127, and are configured to rotate about the extension shafts 125, 127. The rocker devices 128, 130 are coupled to rocker device housings 129, 131, respectively, having a substantially arcuate shape. Each of the housing 129, 131 includes an opening for receiving the distal ends of the extension shafts 125, 127, respectively, which are secured within apertures 124a, 126a of control assembly housing 107a using retaining rings 125d, 127d, which prevent longitudinal movement of the rocker devices 128, 130 while allowing for rotation of the rocker devices 128, 130 within the apertures 124a, 126a. In particular, the rocker device housings 129, 131 prevent longitudinal movement of the rocker devices 128, 130 with respect to the control assembly 107.

With reference to FIGS. 9-11C, 12A-B, and 16A-16B, each of the control shafts 125, 127 includes a bushing 125b, 127b, respectively, which is in contact with springs 125a, 127a disposed within the apertures 124a, 126a of housing 107a. The extension shafts 125, 127 are biased against the rocker devices 128, 130, respectively, by the springs 125a, 127a, which contact the bushings 125b, 127b, which also act as stop members by contacting the distal end of the stems of the rocker devices 128, 130. The bushings 125b, 127b are also in contact with an interior surface of the stems of the rocker devices 128, 130, allowing the extension shafts 125, 127 to move longitudinally with respect to the rocker devices 128, 130 and the rocker devices 128, 130 to rotate with respect to the extension shafts 125, 127 in response to actuation by the user.

Figure 9:
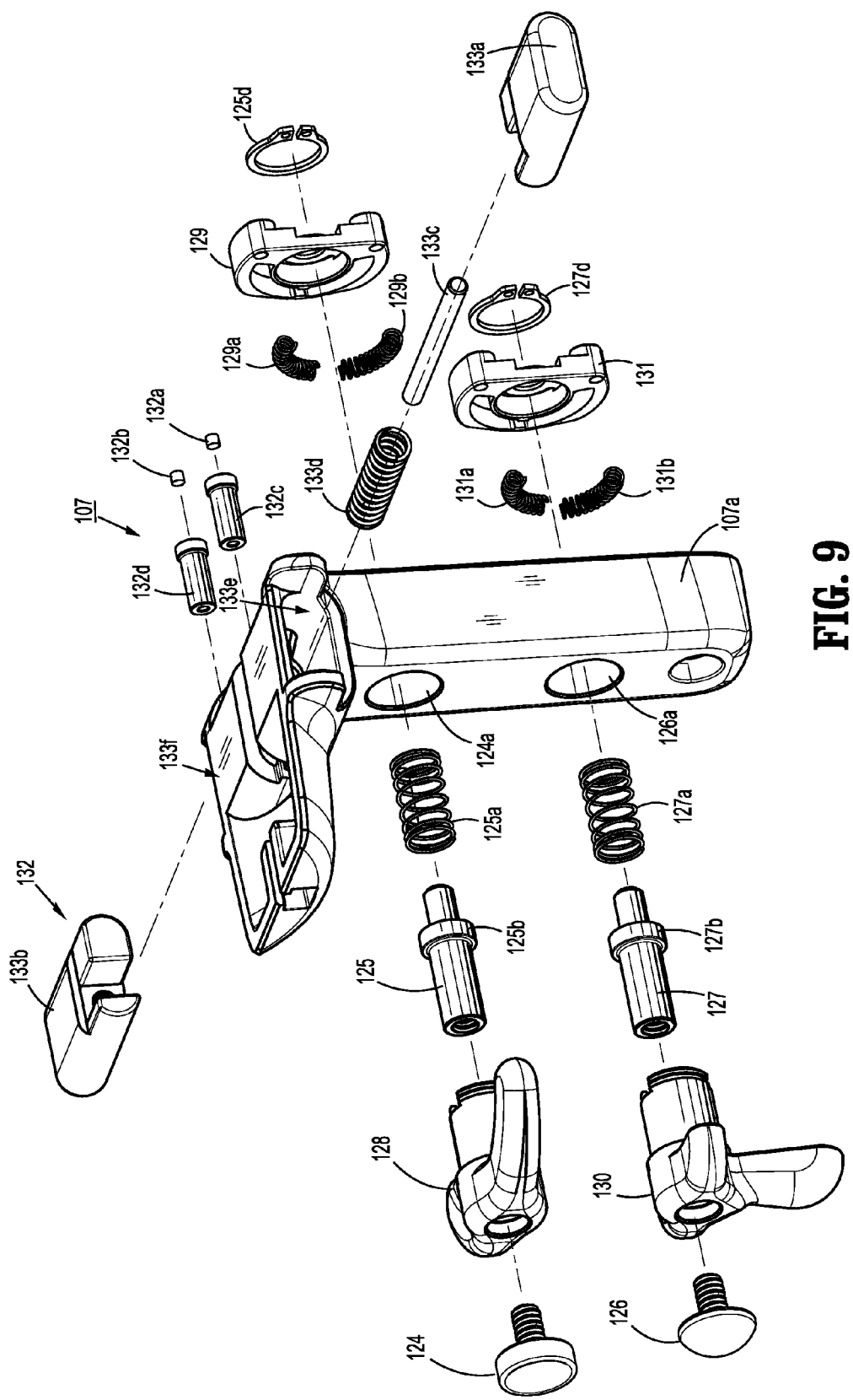
FIG. 9 is a perspective view, with parts separated, of a control assembly of the surgical device of FIGS. 1-3 according to the present disclosure.

With reference to FIG. 9, each of the rocker device housings 129, 131 include a pair of arcuately disposed springs 129a, 129b and 131a, 131b, respectively, which bias the rocker device housings 129, 131 and the rocker devices 128, 130 to a horizontal neutral (e.g., central) position against detents within the housing 107a of control assembly 107. Thus, as the rocker devices 128, 130 are pivoted in a first direction, the springs 129a, 131a are compressed while the springs 129b, 131b are stretched. As the user diminishes and/or terminates the actuation of the rocker devices 128, 130 in the first direction the springs 129a, 131a return the rocker devices 128, 130 to its neutral position at which point the springs 129b, 131b counterbalance the biasing force of the 129a, 131a. Conversely, as the rocker devices 128, 130 are pivoted in a second direction, as viewed from the back of the instrument 100, the springs 129b, 131b are compressed while the springs 129a, 131a are stretched. As the user diminishes and/or terminates the actuation of the rocker devices 128, 130 in the second direction the springs 129b, 131b return the rocker devices 128, 130 to their neutral position at which point the springs 129a, 131a counterbalance the biasing force of the springs 129b, 131b.

Figure 20:
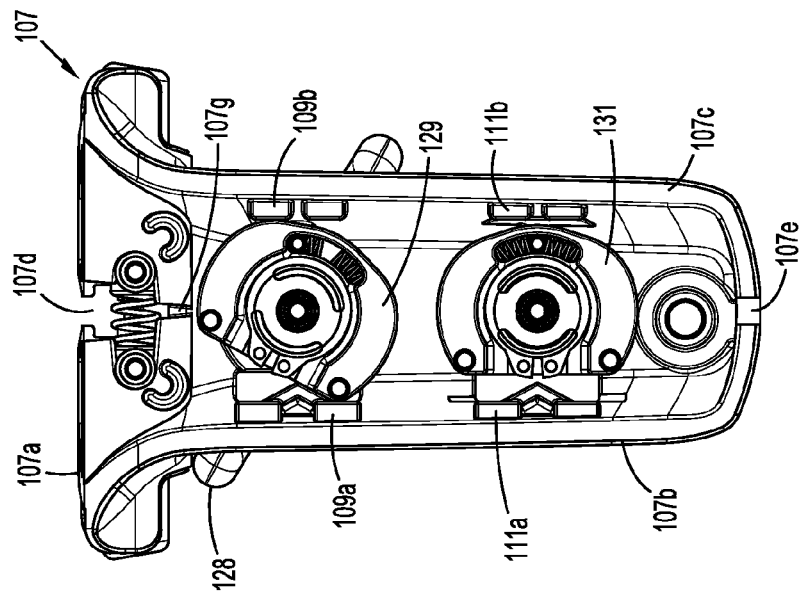
FIG. 20 is a rear, partially-disassembled view of the control assembly of FIG. 9 according to the present disclosure.
Figure 19:
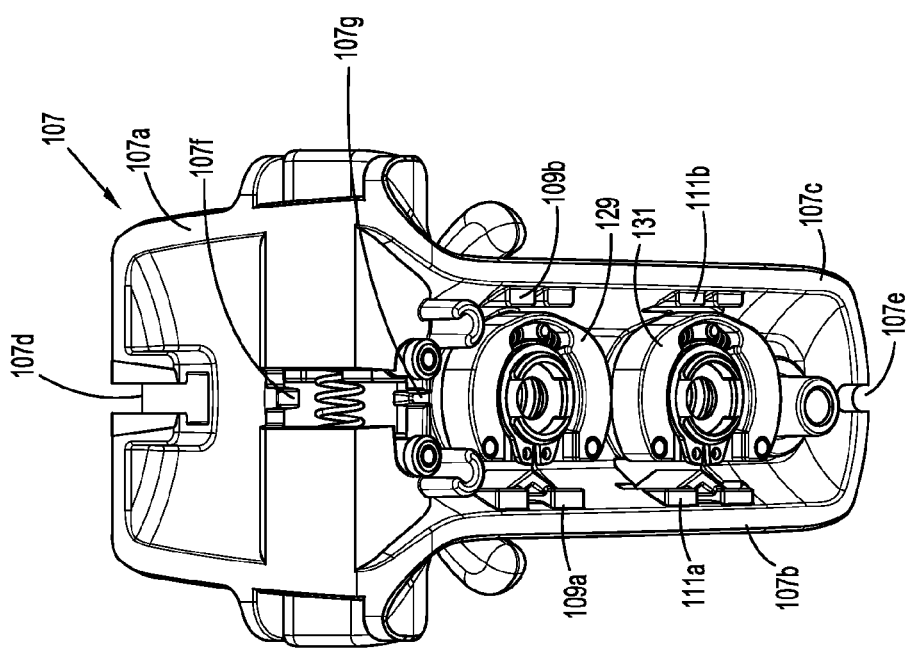
FIG. 19 is a rear, partially-disassembled view of the control assembly of FIG. 9 according to the present disclosure.

With reference to FIGS. 19 and 20, the housing 107a of control assembly 107 includes vertical side walls 107b, 107c having left stop members 109a, 111a and right stop members 109b, 111b. The stop members 109a, 109b and 111a, 111b prevent rotation of the rocker devices 128, 130, respectively, beyond a predetermined limit. As shown in FIG. 20, the stop members 109a, 111a come into contact with flat portions of the rocker device housings 129, 131 while the stop members 109b, 111b come into contact with arcuate portion thereof, thereby preventing rotation of the rocker devices 128, 130.

With continued reference to FIGS. 19 and 20, the housing 107a of control assembly 107 further includes a top drain opening 107d and a lower drain opening 107e disposed above and below, respectively, the control buttons 124, 126 and rocker devices 128, 130. The housing 107a of control assembly 107 further includes one or more interior drain openings 107f and 107g. The openings 107d-g provide for flow of fluids and other contaminants through the housing 107a that may enter the housing 107a during surgery as well as flow of cleaning fluids and gases during sterilization procedures. The configuration of the housing 107a eliminates the need for lubrication and allows for flow-thorough of cleaning and drainage fluids. This also provides an advantage over sealed control assemblies, since sealing of an autoclaveable switch assembly can retain internal pressures or vacuums in functional areas that can inhibit movement of various components.

With reference to FIGS. 9-11C, the control assembly 107 further includes a fire button or safety switch 132 disposed above the control buttons 124, 126 and rocker devices 128, 130. The safety switch 132 includes two opposing switch buttons 133a, 133b disposed within side openings 133d, 133f, respectively, formed in housing 107a. The switch buttons 133a, 133b are slidably coupled to a shaft 133c with a spring 133d disposed about the shaft 133c. The spring 133d biases the switch buttons 133a, 133b against each other pushing the switch buttons 133a, 133b out of the side openings 133d, 133f. During actuation, the user may depress either one of the switch buttons 133a, 133b prior to commencing the firing process as described in further detail below.

In embodiments, the control buttons 124, 126, the rocker devices 128, 130, and switch buttons 133a, 133b may be color-coded to assist the user in selection of the actuators. The control buttons 124, 126, rocker devices 128, 130, and switch buttons 133a, 133b may be subjected to anodization or cold sealing to eliminate color bleeding and/or degradation from auclaving and cleaning procedures.

Each of the control buttons 124, 126, rocker devices 128, 130, and switch buttons 133a, 133b includes magnetic elements 124b, 126b, 128a, 128b, 130a, 130b, 132a, 132b, respectively. The magnetic elements 124b, 126b, 128a, 128b, 130a, 130b, 132a, 132b move in response to actuation of the respective control buttons 124, 126, rocker devices 128, 130, and switch buttons 133a, 133b. The circuit board 150 determines actuation and/or degree of actuation of the control buttons 124, 126, rocker devices 128, 130, and switch buttons 133a, 133b based on relative position of the magnetic elements 124b, 126b, 128a, 128b, 130a, 130b, 132a, 132b relative to corresponding sensors 150a-150g. This allows for control signals to be transmitted to the circuit board 150 without electrical contacts therebetween allowing the circuit board 150 and the control assembly 107 to be housed in any suitable material that allows for transference of magnetic fields.

The magnetic elements 124b, 126b, 128a, 128b, 130a, 130b, 132a, 132b may be formed from any suitable ferromagnetic material, such as samarium cobalt, neodymium, ceramic, ferrite, combinations thereof, and the like and may have any suitable shape, such as, cylindrical, polygonal, (e.g., square or hexagonal cross-section), and the like. The sensors 150a-150g may be any suitable contactless sensors such as Hall Effect sensors, reed switches, ferromagnetic transducers, and the like, that are configured to measure the strength of the magnetic field and/or polarity change of the magnetic elements 124b, 126b, 128a, 128b, 130a, 130b, 132a, 132b. As described above, the control buttons 124, 126, rocker devices 128, 130, and switch buttons 133a, 133b are biased away from the sensors 150a-150g. Actuation by the user moves the magnetic elements 124b, 126b, 128a, 128b, 130a, 130b, 132a, 132b toward and/or in alignment with the sensors 150a-150g. In additional embodiments, the sensors 150a-150g may be triggered in reverse, namely, the triggering process may be reversed by spring biasing the magnetic elements 124b, 126b, 128a, 128b, 130a, 130b, 132a, 132b towards the sensors 150a-150g in their free spring states such that the sensors 150a-150g are triggered "on" and when the controls are actuated, the sensors 150a-150g are triggered "off".

The sensors 150a-150g may be configured as toggle switches that are activated when the amplitudes of the magnetic field strength of the magnetic elements 124b, 126b, 128a, 128b, 130a, 130b, 132a, 132b cross a predetermined threshold through linear or rotational displacement thereof. In embodiments, the sensors 150a-150g may be configured as variable speed sensors by detecting changes in the amplitudes of the magnetic field strength of the magnetic elements 124b, 126b, 128a, 128b, 130a, 130b, 132a, 132b. In further embodiments, the sensors 150a-150g may be configured to measure polarity changes from one or more magnets of the magnetic elements 124b, 126b, 128a, 128b, 130a, 130b, 132a, 132b.

With reference to FIGS. 11A-11C, 14A-B, 16B, and 17A-17B the control buttons 124, 126 are coupled to the respective extension shafts 125, 127 having the respective magnetic elements 124b, 126b, disposed therein. The shafts 125, 127 include cavities 125c, 127c, respectively, for housing the magnetic elements 124b, 126b. In embodiments, the cavities 125c, 127c may include one or more surface features (e.g., ribs) to frictionally engage and secure the magnetic elements 124b, 126b, therein.

Figure 17A:
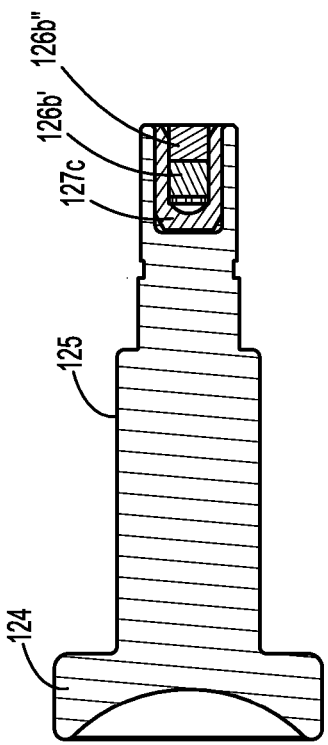
FIG. 17A is a side, cross-sectional view of the control button of FIGS. 14A and 14B with a single magnetic element according to the present disclosure.
Figure 17B:
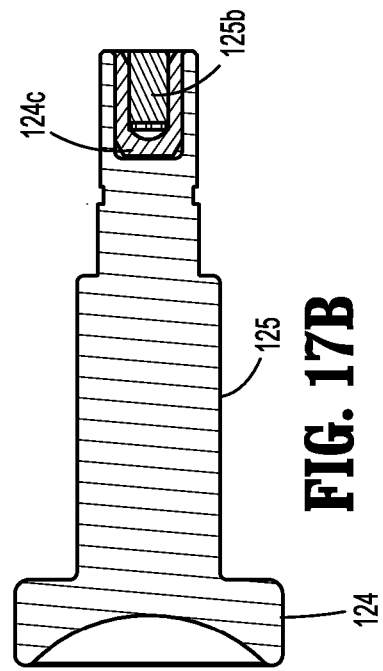
FIG. 17B is a side, cross-sectional view of the control button of FIGS. 14A and 14B with a dual magnetic element according to the present disclosure.

With respect to FIG. 17A, the magnetic element 124b is shown including two portions 124b' and 124b". In embodiments, any of the magnetic elements 124b, 126b, 128a, 128b, 130a, 130b, 132a, 132b may include two portions and for simplicity only the magnetic element 124b is described below. A dual magnet configuration or a magnet having two portions 124b' and 124b" allows for detection of relative position of the magnetic element 124b using polarity shift of the two portions 124b' and 124b" in addition to the strength of the magnetic field as a suitable input method indicative of the position of the control button 124.

Figure 10C:
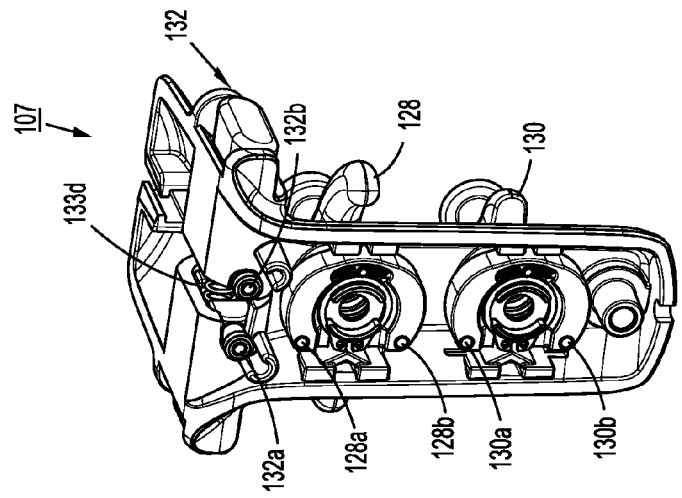
FIG. 10C is a perspective rear view of the control assembly of FIG. 9 according to the present disclosure.
Figure 10B:
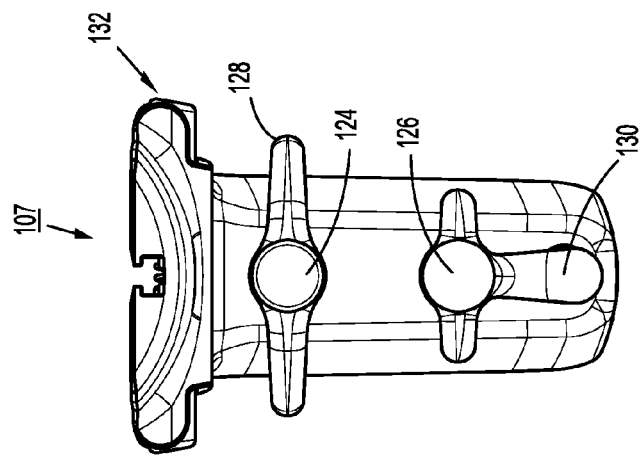
FIG. 10B is a front view of the control assembly of FIG. 9 according to the present disclosure.
Figure 10A:
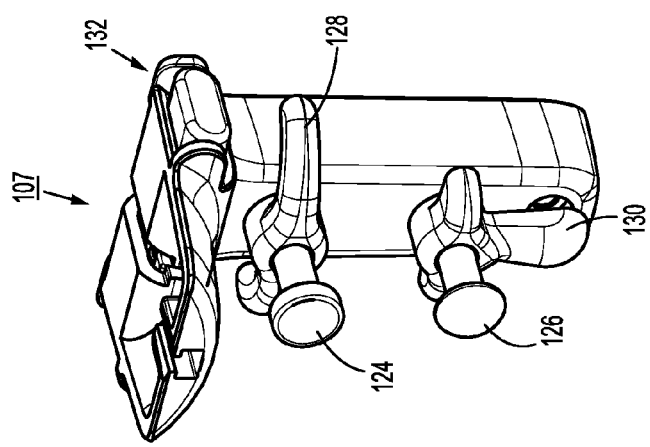
FIG. 10A is a perspective front view of the control assembly of FIG. 9 according to the present disclosure.
Figure 13B:
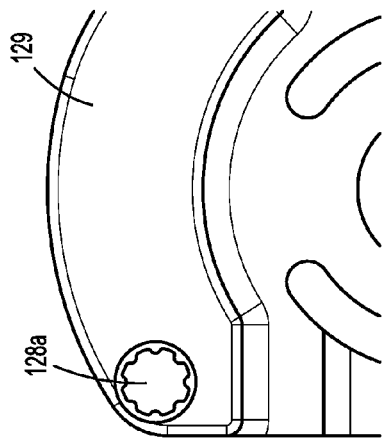
FIG. 13B is a rear view of the rocker switch housing with the magnetic element according to the present disclosure.
Figure 12A:
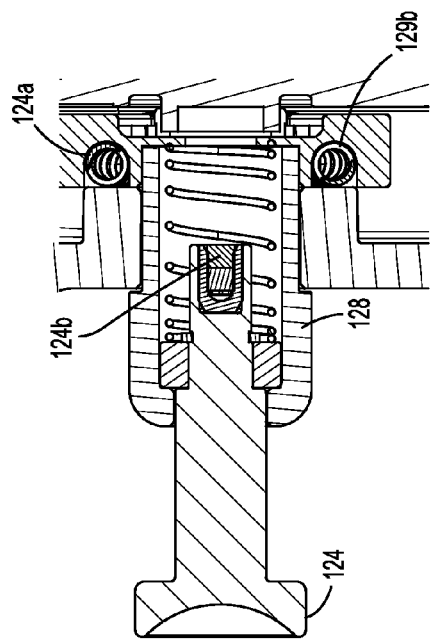
FIG. 12A is an enlarged side, cross-sectional perspective view of the control assembly of FIG. 9 according to the present disclosure.
Figure 13A:
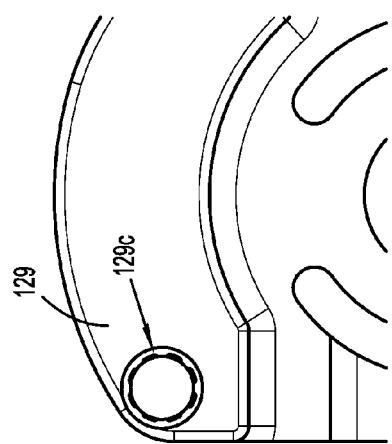
FIG. 13A is a rear view of a rocker switch housing without a magnetic element according to the present disclosure.

With reference to FIGS. 10C and 13A-13B, the rocker device housings 129, 131 include cavities 129c, 129d, and 131c, 131d, respectively. The cavities 129c, 129d, 131c, 131d include the magnetic elements 128a, 128b, 130a, 130b, respectively. In embodiments, the cavities 129c, 129d, 131c, 131d may include one or more surface features (e.g., ribs) to frictionally engage and secure the magnetic elements 124b, 126b, therein.

The cavities (e.g., cavities 125c, 127c, 129c, 129d, 131c, 131d) housing the magnetic elements 124b, 126b, 128a, 128b, 130a, 130b, 132a, 132b may be formed from "sacrificial" (e.g., destructible or deformable) plastic or compliant component materials or geometry that are used for press-fit retention of the magnetic elements 124b, 126b, 128a, 128b, 130a, 130b, 132a, 132b. Magnetic materials are produced primarily using powdered metal manufacturing processes and are inherently fragile. As a result, magnets can crack or be stressed beyond a threshold where their magnetic or ferromagnetic properties are affected or diminished. The plastic or compliant materials or compliant geometries of the cavities of the present disclosure have a lower tensile strength and hardness than the magnets. The magnetic elements 124b, 126b, 128a, 128b, 130a, 130b, 132a, 132b may be retained in a net shape plastic component or in metal components with additional plastic sleeves or inserts with the press-fit feature geometries. This configuration allows for autoclave steam sterilization and is superior to similar press fit geometries with more rigid materials and metals without use of any adhesives. The press fit geometry for the magnets includes features such as ribs, bumps, granular surfaces which act as sacrificial crush members and allow for material displacement in the interspatial regions. The features may be spaced in any suitable configuration, such as evenly spaced around the circumference of the cavities to fit the shape of the magnetic elements 124b, 126b, 128a, 128b, 130a, 130b, 132a, 132b to reduce the overall stress on the magnetic elements 124b, 126b, 128a, 128b, 130a, 130b, 132a, 132b while providing larger tolerance allowances with respect to a full-surface press fit of conventional magnet retention cavities.

Figure 15C:
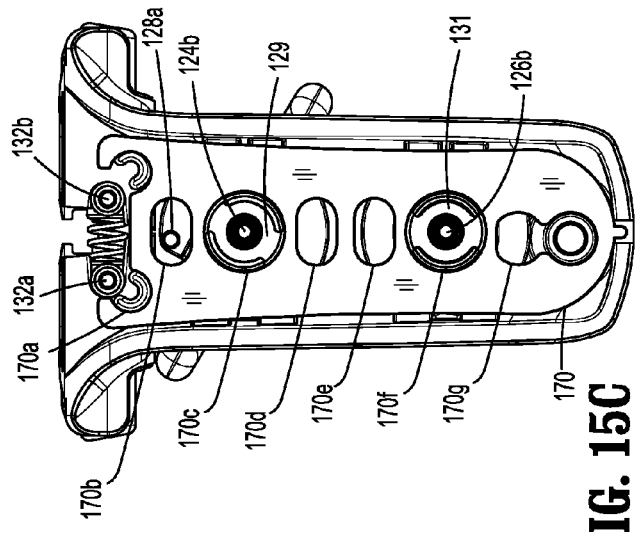
FIGS. 15B and 15C are a rear view of the control assembly of FIG. 9 according to the present disclosure.
Figure 16B:
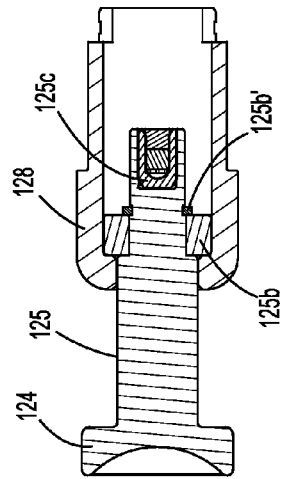
FIG. 16B is a side, cross-sectional view of the control button of FIGS. 14A and 14B and the rocker device according to the present disclosure.
Figure 15B:
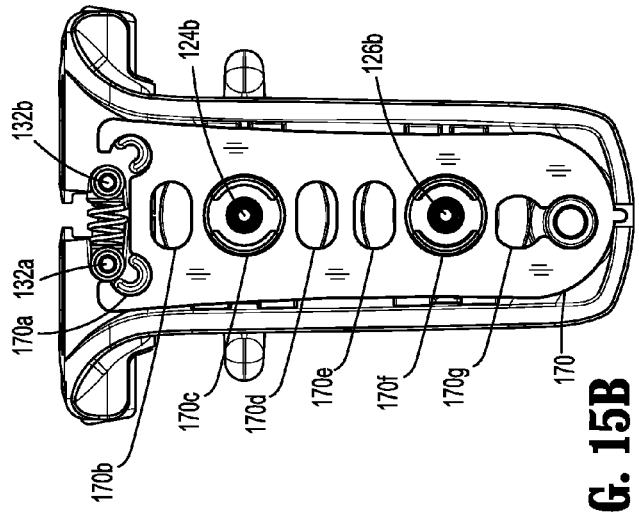
Figure 16A:
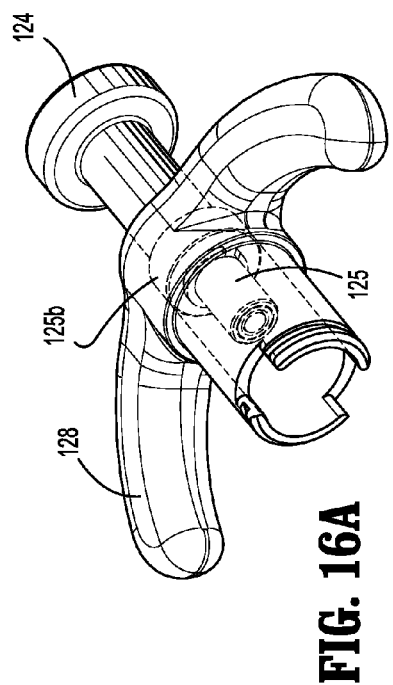
FIG. 16A is a perspective, rear view of the control button of FIGS. 14A and 14B and a rocker device according to the present disclosure.
Figure 18B:
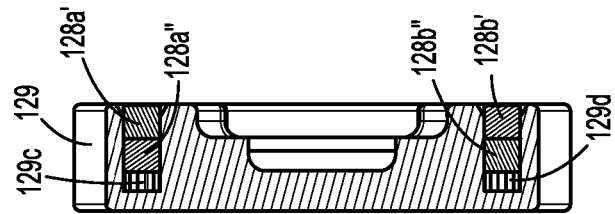
FIG. 18B is a side, cross-sectional view of the rocker switch housing of FIGS. 13A and 13B with a dual magnetic according to the present disclosure.
Figure 18A:
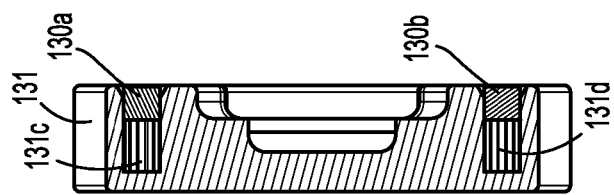
FIG. 18A is a side, cross-sectional view of the rocker switch housing of FIGS. 13A and 13B with a single magnetic according to the present disclosure.

With reference to FIGS. 15A-15C, the control assembly 107 also includes a magnetic shield 170 to selectively control the magnetic field strength and triggering points for the magnetic elements 124b, 126b, 128a, 128b, 130a, 130b, 132a, 132b. In particular, the magnetic shield 170 provides more robust triggering thresholds by localizing the magnetic fields generated by magnetic elements 124b, 126b, 128a, 128b, 130a, 130b, 132a, 132b, which are in close proximity to one another. Suitable materials for forming the magnetic shield 170 include stainless steel alloys, coated/plated steel, and any suitable iron alloys. In embodiments, the magnetic shield 170 may be formed from non-magnetic base materials such as plastics and then plated or coated with ferromagnetic materials. The magnetic shield 170 may have a thickness from about 0.001" to about 0.1", in embodiments from about 0.01" to about 0.05". In further embodiments, the magnetic shield 170 may be formed from a single piece or multiple pieces and may be stationary or include movable components (e.g., shielding elements coupled to the control buttons 124, 126, rocker devices 128, 130, and switch buttons 133a, 133b).

With continued reference to FIGS. 11A-11C and 15A-15C, the magnetic shield 170 includes a plurality of openings 170a-170g allowing for the magnetic elements 124b, 126b, 128a, 128b, 130a, 130b, 132a, 132b to interface with the corresponding sensors 150a-150g as described in the further detail below. In particular, the opening 170a is disposed between the magnetic elements 132a, 132b, and the sensor 150a. The openings 170b and 170d are disposed between with the magnetic elements 128a, 128b and the sensors 150b, 150d only when the magnetic element 128a, 128b are rotated to either first (FIG. 15C) or second directions as described further below, such that while the rocker device 128 is in the neutral configuration (FIG. 15B) the sensors 150b and 150d cannot read the magnetic elements 128a and 128b as they are blocked by the magnetic shield 170. The opening 170c is disposed in proximity with the magnetic element 124b and the sensor 150c.

The openings 170e and 170g are disposed between with the magnetic elements 130a, 130b and the sensors 150e, 150g only when the magnetic element 130a, 130b are rotated to either first or second positions as described below, such that while the rocker device 130 is in the neutral configuration (FIG. 15B) the sensors 150e and 150g cannot read the magnetic elements 130a and 130b as they are blocked by the magnetic shield 170. The opening 170f is disposed between the magnetic element 124b and the sensor 150f.

With reference to FIGS. 7, 10C, and 11A-11C, the circuit board 150 includes the sensors 150a-150g. The sensors 150b and 150d are disposed proximally of the magnetic elements 128a and 128b of the rocker device 128 such that the sensors 150b and 150d sense actuation (e.g., rotation) of the rocker device 128. More specifically, the sensor 150b senses a position of the magnetic element 128a and the sensor 150d senses a position of the magnetic element 128b. As the rocker device 128 is rotated in the first direction the magnetic element 128a is sensed by the sensor 150b and as the rocker device 128 is rotated in the second direction the magnetic element 128b is sensed by the sensor 150d. The activation of sensors 150b and 150d by the rocker device 128, causes circuit board 150 to provide appropriate signals to function selection module 163 and input drive component 165 of drive mechanism 160 to articulate tool assembly 304 relative to body portion 302 of end effector 300. Namely, movement of rocker device 128 in a first direction causes tool assembly 304 to articulate relative to body portion 302 in a first direction, while movement of rocker device 128 in an opposite, e.g., second, direction causes tool assembly 304 to articulate relative to body portion 302 in an opposite, e.g., second, direction.

With continued reference to FIGS. 7 and 11A-11C, the sensor 150c is disposed proximally of the magnetic element 124b of the control button 124 such that the sensor 150c senses actuation (e.g., longitudinal movement) of the control button 124. As the control button 124 is moved distally the magnetic element 124b is sensed by the sensor 150c. The activation of sensor 150c by the control button 124, causes circuit board 150 to provide appropriate signals to function selection module 163 and input drive component 165 of the drive mechanism 160 to close a tool assembly 304 of end effector 300 and/or to fire a stapling/cutting cartridge within tool assembly 304 of end effector 300.

With reference to FIGS. 7, 10C, and 11A-11C, the sensors 150e and 150g are disposed proximally of the magnetic elements 130a and 130b of the rocker device 130 such that the sensors 150e and 150g sense actuation (e.g., rotation) of the rocker device 130. More specifically, the sensor 150e senses a position of the magnetic element 130a and the sensor 150g senses a position of the magnetic element 130b. As the rocker device 130 is rotated in the first direction the magnetic element 130a is sensed by the sensor 150e and as the rocker device 130 is rotated in the section direction the magnetic element 130b is sensed by the sensor 150g. The activation of sensors 150e and 150g by the rocker device 130, causes circuit board 150 to provide appropriate signals to function selection module 163 and input drive component 165 of drive mechanism 160 to rotate end effector 300 relative to handle housing 102 surgical device 100. Specifically, movement of rocker device 130 in a first direction causes end effector 300 to rotate relative to handle housing 102 in a first direction, while movement of rocker device 130 in an opposite, e.g., second, direction causes end effector 300 to rotate relative to handle housing 102 in an opposite, e.g., second, direction.

With continued reference to FIGS. 7 and 11A-11C, the sensor 150f is disposed proximally of the magnetic element 126b of the control button 126 such that the sensor 150f senses actuation (e.g., longitudinal movement) of the control button 126. As the control button 126 is moved distally the magnetic element 126b is sensed by the sensor 150f. The activation of sensor 150f by the control button 126, causes circuit board 150 to provide appropriate signals to function selection module 163 and input drive component 165 of drive mechanism 160 to open tool assembly 304 of end effector 300.

Figure 12B:
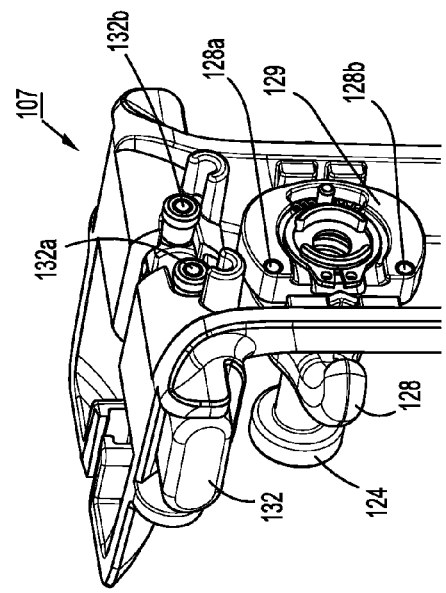
FIG. 12B is an enlarged rear perspective view of the control assembly of FIG. 9 according to the present disclosure.

With reference to FIGS. 9, 10C, and 12B, the switch buttons 133a, 133b include shafts 132c, 132d, coupled thereto having the magnetic elements 132a, 132b, respectively. In embodiments, the shafts 132c, 132d may include cavities (not shown) having one or more surface features (e.g., ribs) to frictionally engage and secure the magnetic elements 132a, 132b, therein. The sensor 150a is disposed proximally of the magnetic elements 132a, 132b and on the same horizontal plane as the magnetic elements 132a, 132b. The sensor 150a senses actuation of one or both of the switch buttons 133a, 133b signaling to the circuit 150 that the end effector 300 may be fired once the control button 124 is actuated. Thus, as one of the switch buttons 133a, 133b is actuated following the actuation of the control button 124, the circuit board 150 provides appropriate signals to function selection module 163 and input drive component 165 of the drive mechanism 160 to fire a stapling/cutting cartridge within tool assembly 304 of end effector 300.

Reference may be made to U.S. Patent Publication No. 2009/0314821, filed on Aug. 31, 2009, entitled "TOOL ASSEMBLY FOR A SURGICAL STAPLING DEVICE," the entire content of which is incorporated herein by reference, for a detailed discussion of the construction and operation of end effector 300.

Reference may also be made to U.S. patent application Ser. No. 13/484,975, filed on May 31, 2012, entitled "HAND HELD SURGICAL HANDLE ASSEMBLY, SURGICAL ADAPTERS FOR USE BETWEEN SURGICAL HANDLE ASSEMBLY AND SURGICAL END EFFECTORS, AND METHODS OF USE", the entire content of which is incorporated herein by reference, for a detailed discussion of the construction and operation of any of the remaining components of surgical device 100, adapter assembly 200, and end effector 300.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. A surgical device, comprising:
   a jaw assembly defining a first longitudinal axis and including a first jaw and a second jaw moveable relative to the first jaw;
   an elongated body defining a second longitudinal axis and coupled to a proximal end of the jaw assembly, wherein the jaw assembly is configured to articulate about an articulation axis transverse to the second longitudinal axis relative to the elongated body;
   a handle assembly coupled to a proximal end of the elongated body and comprising at least one motor mechanically coupled to the jaw assembly; and
   a control assembly coupled to the handle assembly, the control assembly including:
      a first control button;
      a second control button;
      a first rocker device defining a first aperture therethrough configured to receive a portion of the first control button therein; and
      a second rocker device defining a second aperture therethrough configured to receive a portion of the second control button therein,
      wherein the first and second rocker devices are rotatably supported on the first and second control buttons, respectively.

2. The surgical device according to claim 1, wherein actuation of the first control button moves the second jaw in approximation relative to the first jaw and actuating the second control button moves the second jaw away from the first jaw.

3. The surgical device according to claim 1, wherein actuation of the first rocker device is configured to articulate the jaw assembly about the articulation axis.

4. The surgical device according to claim 1, wherein actuation of the second rocker device is configured to rotate the jaw assembly about the second longitudinal axis relative to the elongated body.

5. The surgical device according to claim 1, wherein the first control button includes a first magnetic element, the second control button includes a second magnetic element, the first rocker device includes third and fourth magnetic elements, and the second rocker device includes fifth and sixth magnetic elements.

6. The surgical device according to claim 5, wherein the handle assembly comprises a plurality of sensors configured to detect proximity of the first, second, third, fourth, fifth, and sixth magnetic elements.

7. The surgical device according to claim 6, wherein the control assembly comprises a magnetic shield having a plurality of openings aligned with the plurality of sensors, the magnetic shield configured to shield the third, fourth, fifth, and sixth magnetic elements from respective sensors until the first and second rocker devices are actuated.

* * * * *